United States Patent
Raffle et al.

(10) Patent No.: US 8,506,080 B2
(45) Date of Patent: * Aug. 13, 2013

(54) UNLOCKING A SCREEN USING EYE TRACKING INFORMATION

(75) Inventors: Hayes Solos Raffle, Palo Alto, CA (US); Adrian Wong, Mountain View, CA (US); Ryan Geiss, San Jose, CA (US)

(73) Assignee: Google Inc., Mountain View, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/539,532

(22) Filed: Jul. 2, 2012

(65) Prior Publication Data

US 2013/0135204 A1    May 30, 2013

Related U.S. Application Data

(63) Continuation of application No. 13/307,452, filed on Nov. 30, 2011, now Pat. No. 8,235,529.

(51) Int. Cl.
*A61B 3/14* (2006.01)
(52) U.S. Cl.
USPC .......................................... 351/209; 351/210
(58) Field of Classification Search
USPC ................................................ 351/200–246
See application file for complete search history.

(56) References Cited

U.S. PATENT DOCUMENTS

| | | | |
|---|---|---|---|
| 5,689,619 A * | 11/1997 | Smyth | 706/45 |
| 6,396,497 B1 | 5/2002 | Reichlen | |
| 7,479,949 B2 | 1/2009 | Jobs et al. | |
| 7,986,816 B1 | 7/2011 | Hoanca | |
| 8,235,529 B1 * | 8/2012 | Raffle et al. | 351/209 |
| 2001/0043402 A1 | 11/2001 | Melville | |
| 2006/0115130 A1 | 6/2006 | Kozlay | |
| 2007/0057842 A1 * | 3/2007 | Coleman et al. | 342/359 |
| 2008/0122796 A1 | 5/2008 | Jobs et al. | |

* cited by examiner

*Primary Examiner* — Mohammed Hasan
(74) *Attorney, Agent, or Firm* — McDonnell Boehnen Hulbert & Berghoff LLP (57) ABSTRACT

Methods and systems for unlocking a screen using eye tracking information are described. A computing system may include a display screen. The computing system may be in a locked mode of operation after a period of inactivity by a user. Locked mode of operation may include a locked screen and reduced functionality of the computing system. The user may attempt to unlock the screen. The computing system may generate a display of a moving object on the display screen of the computing system. An eye tracking system may be coupled to the computing system. The eye tracking system may track eye movement of the user. The computing system may determine that a path associated with the eye movement of the user substantially matches a path associated with the moving object on the display and switch to be in an unlocked mode of operation including unlocking the screen.

19 Claims, 8 Drawing Sheets

COMPUTER PROGRAM PRODUCT 800

SIGNAL BEARING MEDIUM 801

PROGRAM INSTRUCTIONS 802

- GENERATING A DISPLAY OF A MOVING OBJECT ON A DISPLAY OF A COMPUTING SYSTEM, WHEREIN THE COMPUTING SYSTEM IS OPERABLE TO BE IN A LOCKED MODE OF OPERATION

- RECEIVING INFORMATION ASSOCIATED WITH EYE MOVEMENT OF A USER OF THE COMPUTING SYSTEM

- BASED ON THE INFORMATION ASSOCIATED WITH THE EYE MOVEMENT, DETERMINING THAT A PATH ASSOCIATED WITH THE EYE MOVEMENT SUBSTANTIALLY MATCHES A PATH OF THE MOVING OBJECT

- IN RESPONSE TO DETERMINING THAT THE PATH ASSOCIATED WITH THE EYE MOVEMENT SUBSTANTIALLY MATCHES THE PATH OF THE MOVING OBJECT, CAUSING THE COMPUTING SYSTEM TO SWITCH FROM BEING IN THE LOCKED MODE OF OPERATION TO BEING IN AN UNLOCKED MODE OF OPERATION, WHEREIN FUNCTIONALITY OF THE COMPUTING SYSTEM IS REDUCED IN THE LOCKED MODE AS COMPARED TO IN THE UNLOCKED MODE.

| COMPUTER READABLE MEDIUM 803 | COMPUTER RECORDABLE MEDIUM 804 | COMMUNICATIONS MEDIUM 805 |
|---|---|---|

FIGURE 8

UNLOCKING A SCREEN USING EYE TRACKING INFORMATION

CROSS REFERENCE TO RELATED APPLICATION

The present application is a continuation of U.S. patent application Ser. No. 13/307,452, filed on Nov. 30, 2011, and entitled "Unlocking a Screen Using Eye Tracking Information," which is herein incorporated by reference as if fully set forth in this description.

BACKGROUND

Wearable computers include electronic devices that may be worn by a user. As examples, wearable computers can be under or on top of clothing or integrated into eye glasses. There may be constant interaction between a wearable computer and a user. The wearable computer may be integrated into user activities and may be considered an extension of the mind and/or body of the user.

The wearable computer may include an image display element close enough to an eye of a wearer such that a displayed image fills or nearly fills a field of view associated with the eye, and appears as a normal sized image, such as might be displayed on a traditional image display device. The relevant technology may be referred to as "near-eye displays." Near-eye displays may be integrated into wearable displays, also sometimes called "head-mounted displays" (HMDs).

SUMMARY

The present application discloses systems and methods to unlock a screen using eye tracking information. In one aspect, a method is described. The method may comprise generating a display of a moving object on a display of a computing system. The computing system may be operable to be in a locked mode of operation and may include an eye tracking system. The method may also comprise receiving information associated with eye movement of a user of the computing system from the eye tracking system. Based on the information associated with the eye movement, the method may further comprise determining that a path associated with the eye movement substantially matches a path of the moving object. In response to determining that the path associated with the eye movement substantially matches the path of the moving object, the method may comprise causing the computing system to switch from being in the locked mode of operation to being in an unlocked mode of operation. Functionality of the computing system may be reduced in the locked mode as compared to the unlocked mode.

In another aspect, a computer readable memory having stored therein instructions executable by a computing device to cause the computing device to perform functions is described. The functions may comprise generating a display of a moving object on a display of a computing system. The computing system may be operable to be in a locked mode of operation and may include an eye tracking system. The functions may also comprise receiving information associated with eye movement of a user of the computing system from the eye tracking system. Based on the information associated with the eye movement, the function may further comprise determining that a path associated with the eye movement substantially matches a path of the moving object. In response to determining that the path associated with the eye movement substantially matches the path of the moving object, the functions may comprise causing the computing system to switch from being in the locked mode of operation to being in an unlocked mode of operation. Functionality of the computing system may be reduced in the locked mode as compared to the unlocked mode.

In still another aspect, a system is described. The system may comprise a wearable computer including a head-mounted display (HMD). The wearable computer may be operable to be in a locked mode of operation. The system may also comprise an eye tracking system in communication with the wearable computer. The eye tracking system may be configured to track eye movement of a user of the wearable computer. The system may further comprise a processor in communication with the wearable computer and the eye tracking system. The processor may be configured to generate a display of a text on a display of the HMD and to receive information associated with eye movement from the eye tracking system. Based on the information associated with the eye movement, the processor may be configured to determine that the eye movement is associated with reading the text. In response to determining that the eye movement is associated with reading the text, the processor may further be configured to cause the wearable computer to switch from being in the locked mode of operation to being in an unlocked mode of operation. Functionality of the wearable computer may be reduced in the locked mode as compared to the unlocked mode.

In yet another aspect, a method is described. The method may comprise generating a display of a moving object on a head-mounted display (HMD) coupled to a wearable computing system. The wearable computing system may include an eye tracking system. The method may also comprise receiving information associated with eye movement of a user of the HMD from the eye tracking system. The method may further comprise determining a relative location of a gaze axis of an eye of the user of the HMD with respect to a reference axis associated with the HMD. Based on the relative location of the gaze axis of the eye of the user of the HMD with respect to the reference axis associated with the HMD, the method may comprise determining calibration parameters. The calibration parameters may be associated with causing a path associated with the eye movement of the user to substantially match a path of the moving object.

The foregoing summary is illustrative only and is not intended to be in any way limiting. In addition to the illustrative aspects, embodiments, and features described above, further aspects, embodiments, and features will become apparent by reference to the figures and the following detailed description.

DETAILED DESCRIPTION

The following detailed description describes various features and functions of the disclosed systems and methods with reference to the accompanying figures. In the figures, similar symbols identify similar components, unless context dictates otherwise. The illustrative system and method embodiments described herein are not meant to be limiting. It may be readily understood that certain aspects of the disclosed systems and methods can be arranged and combined in a wide variety of different configurations, all of which are contemplated herein.

This disclosure may disclose, inter alia, systems and methods for unlocking a screen using eye tracking information. A computing system may include a display screen. The computing system may be operable to be in a locked mode of operation after a period of inactivity by a user. Locked mode of operation may include a locked screen and reduced functionality of the computing system. The user may attempt to unlock the screen. The computing system may generate a display of a moving object on the display screen of the computing system. An eye tracking system may be coupled to the computing system. The eye tracking system may track eye movement of the user. The computing system may determine that a path associated with the eye movement of the user substantially matches a path associated with the moving object on the display and switch to be in an unlocked mode of operation including unlocking the screen.

The computing system may include a wearable computing system. The wearable computing system may include a head-mounted display (HMD). In some examples, the wearable computing system may or may not include or be coupled to a mouse or a convenient keyboard that can be used to unlock a screen of the HMD after a period of inactivity of a wearer of the HMD.

To unlock a screen coupled to the HMD after a period of inactivity that may have caused the screen to be locked, a processor coupled to the wearable computing system may generate a display of a moving object and detect through an eye tracking system if an eye of the wearer may be tracking the moving object. The processor may determine that a path associated with the movement of the eye of the wearer matches or substantially matches a path of the moving object and may unlock the display. The path of the moving object may be randomly generated and may be different every time the wearer attempts to unlock the screen. Tracking a slowly moving object may reduce a probability of eye blinks, or rapid eye movements (i.e., saccades) disrupting the eye tracking system. The processor may generate the display of the moving object such that a speed associated with motion of the moving object on the HMD may be less than a predetermined threshold speed. Onset of rapid eye pupil movements may occur if a speed of a moving object tracked by the eye of the wearer is equal to or greater than the predetermined threshold speed. Alternatively, the speed associated with the moving object may be independent of correlation to eye blinks or rapid eye movements. The speed associated with the motion of the moving object may change, i.e., the moving object may accelerate or decelerate. The processor may track the eye movement of the eye of the wearer to detect if the eye movement may indicate that the eye movement may be correlated with changes in the speed associated with the motion of the moving object and may unlock the screen accordingly.

Alternative to the processor generating the display of the moving object on the HMD, the processor may cause an image or a sequence of images including the moving object to be projected on a retina of the eye of the wearer and may determine if the eye pupil of the wearer may be tracking the moving object in the sequence of images, for example.

In another example, the processor may generate a display of or render a static path (e.g., a Z shape, part of a circle, etc.) on the HMD. The processor may determine, through the eye tracking system, if wearer may be tracing the static path with the eye pupil of the wearer, for example, and unlock the screen. The static path may be less distracting to the wearer than a continuous display of the moving object in a peripheral vision of the wearer. Also, the static path can be displayed on a low-power display, while a dynamic moving object may require a high-power display. The low-power display may be used to unlock the screen, while the high-power display may be turned off until the screen may be unlocked to save power.

In still another example, unlocking a display coupled to a computing system may include generating a display of series of discrete targets flashing on the display. Each target may appear on the display and then disappear from the display within a period of time, i.e., the targets may flash at predetermined intervals of time (e.g., 200 ms). A processor coupled to the computing system may track an eye of a user of the computing system and compare gaze locations of the eye of the user to predetermined locations of the discrete targets flashing on the display. If the gaze locations of the eye of the user substantially match and predetermined locations of the discrete targets flashing on the display, the display may be unlocked, for example.

In yet another example, the wearable computer may generate a display of a text and may detect through an eye tracking system if eye movement of an eye of a user may indicate that the user may be reading the text. The wearable computer may determine that gaze movements associated with eye movement substantially match a predetermined special-temporal pattern of gaze locations associated with reading the text on the display and may unlock the screen.

The eye tracking system may comprise a camera that may continuously be enabled to monitor eye movement. The wearable computer may alternatively include a sensor consuming less electric power than the camera to detect a user attempt to unlock the display screen and then enable the camera to cause the eye tracking system to be operable. The wearer may perform a gesture to indicate an attempt to unlock the HMD screen. For example, a gyroscope coupled to the HMD may detect a head tilt, for example, and indicate that the wearer may be attempting to unlock the HMD screen.

I. Example Wearable Computing and Head Mounted Display System

Figure 1:
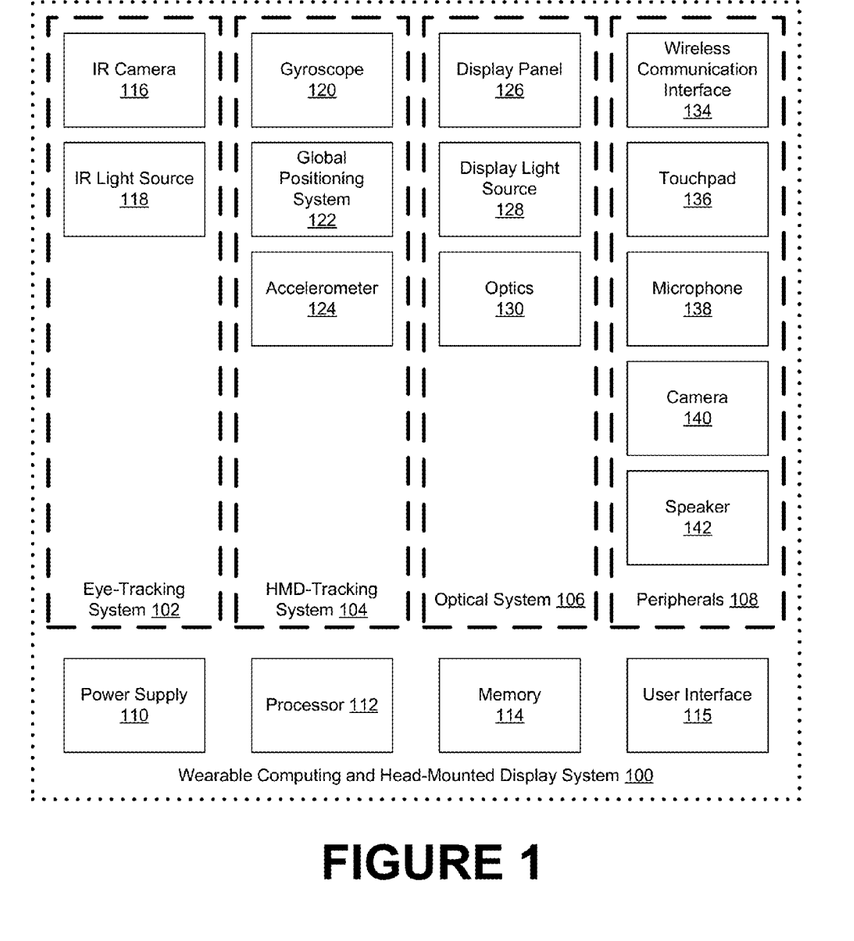
FIG. 1 is a block diagram of an example wearable computing and head-mounted display system, in accordance with an example embodiment.

FIG. 1 is a block diagram of an example wearable computing and head-mounted display (HMD) system 100 that may include several different components and subsystems. Components coupled to or included in the system 100 may include an eye-tracking system 102, a HMD-tracking system 104, an optical system 106, peripherals 108, a power supply 110, a processor 112, a memory 114, and a user interface 115. Components of the system 100 may be configured to work in an interconnected fashion with each other and/or with other components coupled to respective systems. For example, the power supply 110 may provide power to all the components of the system 100. The processor 112 may receive information from and control the eye tracking system 102, the HMD-tracking system 104, the optical system 106, and peripherals 108. The processor 112 may be configured to execute program instructions stored in the memory 114 and to generate a display of images on the user interface 115.

The eye-tracking system 102 may include hardware such as an infrared camera 116 and at least one infrared light source 118. The infrared camera 116 may be utilized by the eye-tracking system 102 to capture images of an eye of the wearer. The images may include either video images or still images or both. The images obtained by the infrared camera 116 regarding the eye of the wearer may help determine where the wearer may be looking within a field of view of the HMD included in the system 100, for instance, by ascertaining a location of the eye pupil of the wearer. The infrared camera 116 may include a visible light camera with sensing capabilities in the infrared wavelengths.

The infrared light source 118 may include one or more infrared light-emitting diodes or infrared laser diodes that may illuminate a viewing location, i.e. an eye of the wearer. Thus, one or both eyes of a wearer of the system 100 may be illuminated by the infrared light source 118. The infrared light source 118 may be positioned along an optical axis common to the infrared camera, and/or the infrared light source 118 may be positioned elsewhere. The infrared light source 118 may illuminate the viewing location continuously or may be turned on at discrete times.

The HMD-tracking system 104 may include a gyroscope 120, a global positioning system (GPS) 122, and an accelerometer 124. The HMD-tracking system 104 may be configured to provide information associated with a position and an orientation of the HMD to the processor 112. The gyroscope 120 may include a microelectromechanical system (MEMS) gyroscope or a fiber optic gyroscope as examples. The gyroscope 120 may be configured to provide orientation information to the processor 112. The GPS unit 122 may include a receiver that obtains clock and other signals from GPS satellites and may be configured to provide real-time location information to the processor 112. The HMD-tracking system 104 may further include an accelerometer 124 configured to provide motion input data to the processor 112.

The optical system 106 may include components configured to provide images to a viewing location, i.e. an eye of the wearer. The components may include a display panel 126, a display light source 128, and optics 130. These components may be optically and/or electrically-coupled to one another and may be configured to provide viewable images at a viewing location. One or two optical systems 106 may be provided in the system 100. In other words, the HMD wearer may view images in one or both eyes, as provided by one or more optical systems 106. Also, the optical system(s) 106 may include an opaque display and/or a see-through display coupled to the display panel 126, which may allow a view of the real-world environment while providing superimposed virtual images. The infrared camera 116 coupled to the eye tracking system 102 may be integrated into the optical system 106.

Additionally, the system 100 may include or be coupled to peripherals 108, such as a wireless communication interface 134, a touchpad 136, a microphone 138, a camera 140, and a speaker 142. Wireless communication interface 134 may use 3G cellular communication, such as CDMA, EVDO, GSM/GPRS, or 4G cellular communication, such as WiMAX or LTE. Alternatively, wireless communication interface 134 may communicate with a wireless local area network (WLAN), for example, using WiFi. In some examples, wireless communication interface 134 may communicate directly with a device, for example, using an infrared link, Bluetooth, near field communication, or ZigBee.

The power supply 110 may provide power to various components in the system 100 and may include, for example, a rechargeable lithium-ion battery. Various other power supply materials and types known in the art are possible.

The processor 112 may execute instructions stored in a non-transitory computer readable medium, such as the memory 114, to control functions of the system 100. Thus, the processor 112 in combination with instructions stored in the memory 114 may function as a controller of system 100. For example, the processor 112 may control the wireless communication interface 134 and various other components of the system 100. In other examples, the processor 112 may include a plurality of computing devices that may serve to control individual components or subsystems of the system 100. Analysis of the images obtained by the infrared camera 116 may be performed by the processor 112 in conjunction with the memory 114.

In addition to instructions that may be executed by the processor 112, the memory 114 may store data that may include a set of calibrated wearer eye pupil positions and a collection of past eye pupil positions. Thus, the memory 114 may function as a database of information related to gaze direction. Calibrated wearer eye pupil positions may include, for instance, information regarding extents or range of an eye pupil movement (right/left and upwards/downwards), and relative position of eyes of the wearer with respect to the HMD. For example, a relative position of a center and corners of an HMD screen with respect to a gaze direction or a gaze angle of the eye pupil of the wearer may be stored. Also, locations or coordinates of starting and ending points, or waypoints, of a path of a moving object displayed on the HMD, or of a static path (e.g., semicircle, Z-shape etc.) may be stored on the memory 114.

The system 100 may further include the user interface 115 for providing information to the wearer or receiving input from the wearer. The user interface 115 may be associated with, for example, displayed images, a touchpad, a keypad, buttons, a microphone, and/or other peripheral input devices. The processor 112 may control functions of the system 100 based on input received through the user interface 115. For example, the processor 112 may utilize user input from the user interface 115 to control how the system 100 may display images within a field of view or may determine what images the system 100 may display.

Although FIG. 1 shows various components of the system 100 (i.e., wireless communication interface 134, processor 112, memory 114, infrared camera 116, display panel 126, GPS 122, and user interface 115) as being integrated into the system 100, one or more of the described functions or components of the system 100 may be divided up into additional functional or physical components, or combined into fewer functional or physical components. For example, the infrared camera 116 may be mounted on the wearer separate from the system 100. Thus, the system 100 may be part of a wearable computing device in the form of separate devices that can be worn on or carried by the wearer. Separate components that make up the wearable computing device may be communicatively coupled together in either a wired or wireless fashion. In some further examples, additional functional and/or physical components may be added to the examples illustrated by FIG. 1. In other examples, the system 100 may be included within other systems.

The system 100 may be configured as, for example, eyeglasses, goggles, a helmet, a hat, a visor, a headband, or in some other form that can be supported on or from a head of the wearer. The system 100 may be further configured to display images to both eyes of the wearer. Alternatively, the system 100 may display images to only one eye, either a left eye or a right eye.

II. Example Head Mounted Display Integrated into Eyeglasses

Figure 2A:
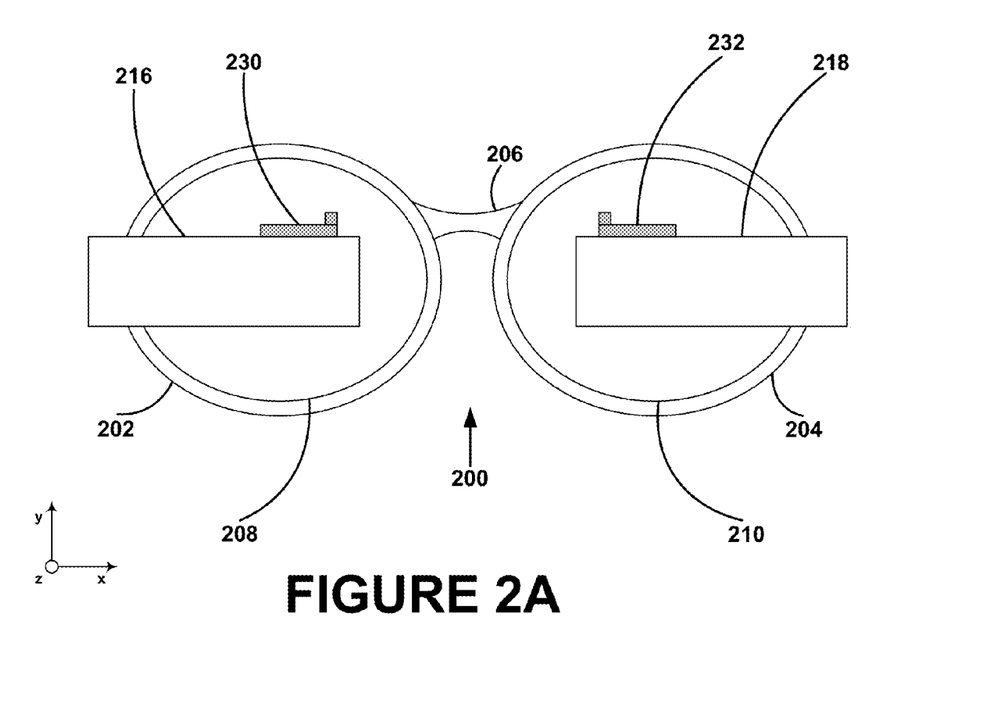
FIG. 2A illustrates a front view of a head-mounted display (HMD) in an example eyeglasses embodiment that includes a head-mounted support.
Figure 2B:
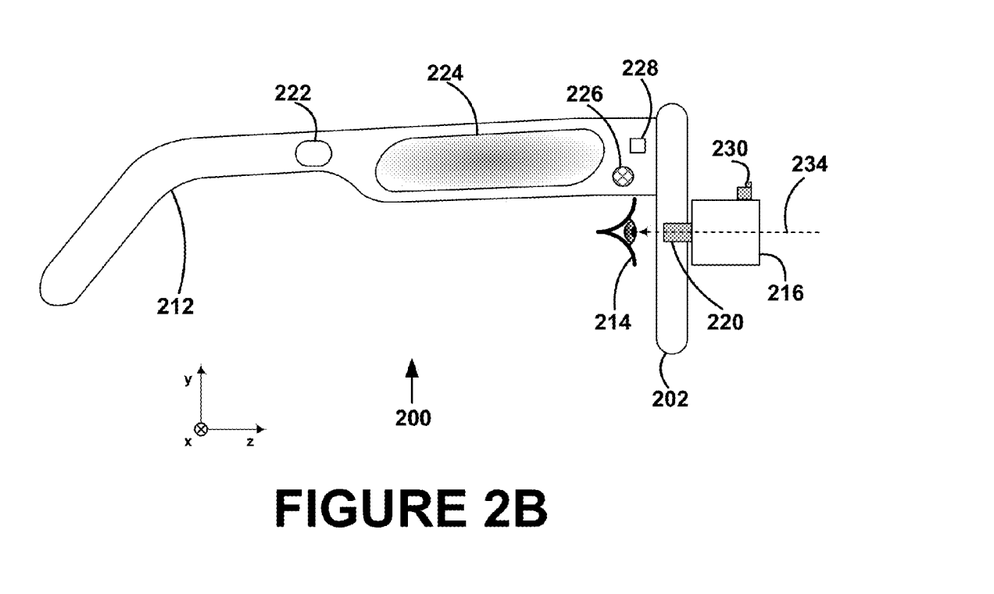
FIG. 2B illustrates a side view of the HMD in the example eyeglasses embodiment.

FIG. 2A illustrates a front view of a head-mounted display (HMD) 200 in an example eyeglasses embodiment. FIG. 2B presents a side view of the HMD 200 in FIG. 2A. FIGS. 2A and 2B will be described together. Although this example embodiment is provided in an eyeglasses format, it will be understood that wearable systems and HMDs may take other forms, such as hats, goggles, masks, headbands and helmets. The HMD 200 includes lens frames 202 and 204, a center frame support 206, lens elements 208 and 210, and an extending side-arm 212 that may be affixed to the lens frame 202. There may be another extending side arm affixed to the lens frame 204 but is not shown. The center frame support 206 and side-arm 212 may be configured to secure the HMD 200 to a head of a wearer via a nose and an ear of the wearer. Each of the frame elements 202, 204, and 206 and the extending side-arm 212 may be formed of a solid structure of plastic or metal, or may be formed of a hollow structure of similar material so as to allow wiring and component interconnects to be internally routed through the HMD 200. Lens elements 208 and 210 may be at least partially transparent so as to allow the wearer to look through lens elements. In particular, a right eye 214 of the wearer may look through right lens 210. Optical systems 216 and 218 may be positioned in front of lenses 208 and 210, respectively. The optical systems 216 and 218 may be attached to the HMD 200 using support mounts such as 220 shown for the right optical system 216. Furthermore, the optical systems 216 and 218 may be integrated partially or completely into lens elements 208 and 210, respectively.

Although FIG. 2A illustrates an optical system for each eye, the HMD 200 may include an optical system for only one eye (e.g., right eye 214). The wearer of the HMD 200 may simultaneously observe from optical systems 216 and 218 a real-world image with an overlaid displayed image. The HMD 200 may include various elements such as a processor 222, a touchpad 224, a microphone 226, and a button 228. The processor 222 may use data from, among other sources, various sensors and cameras to determine a displayed image that may be displayed to the wearer. The HMD 200 may also include eye tracking systems 230 and 232 that may be integrated into the optical systems 216 and 218, respectively. The location of eye tracking systems 230 and 232 is for illustration only. The eye tracking systems 230 and 232 may be positioned in different locations and may be separate or attached to the HMD 200. A gaze axis or direction 234 associated with the eye 214 may be shifted or rotated with respect to the optical system 216 or eye tracking system 230 depending on placement of the HMD 200 on the nose and ears of the wearer. The eye-tracking systems 230 and 232 may include hardware such as an infrared camera and at least one infrared light source, but may include other components also. In one example, an infrared light source or sources integrated into the eye tracking system 230 may illuminate the eye 214 of the wearer, and a reflected infrared light may be collected with an infrared camera to track eye or eye-pupil movement. Those skilled in the art would understand that other user input devices, user output devices, wireless communication devices, sensors, and cameras may be reasonably included in such a wearable computing system.

III. Example Methods to Unlock a Screen Using Eye Tracking Information

Figure 3:
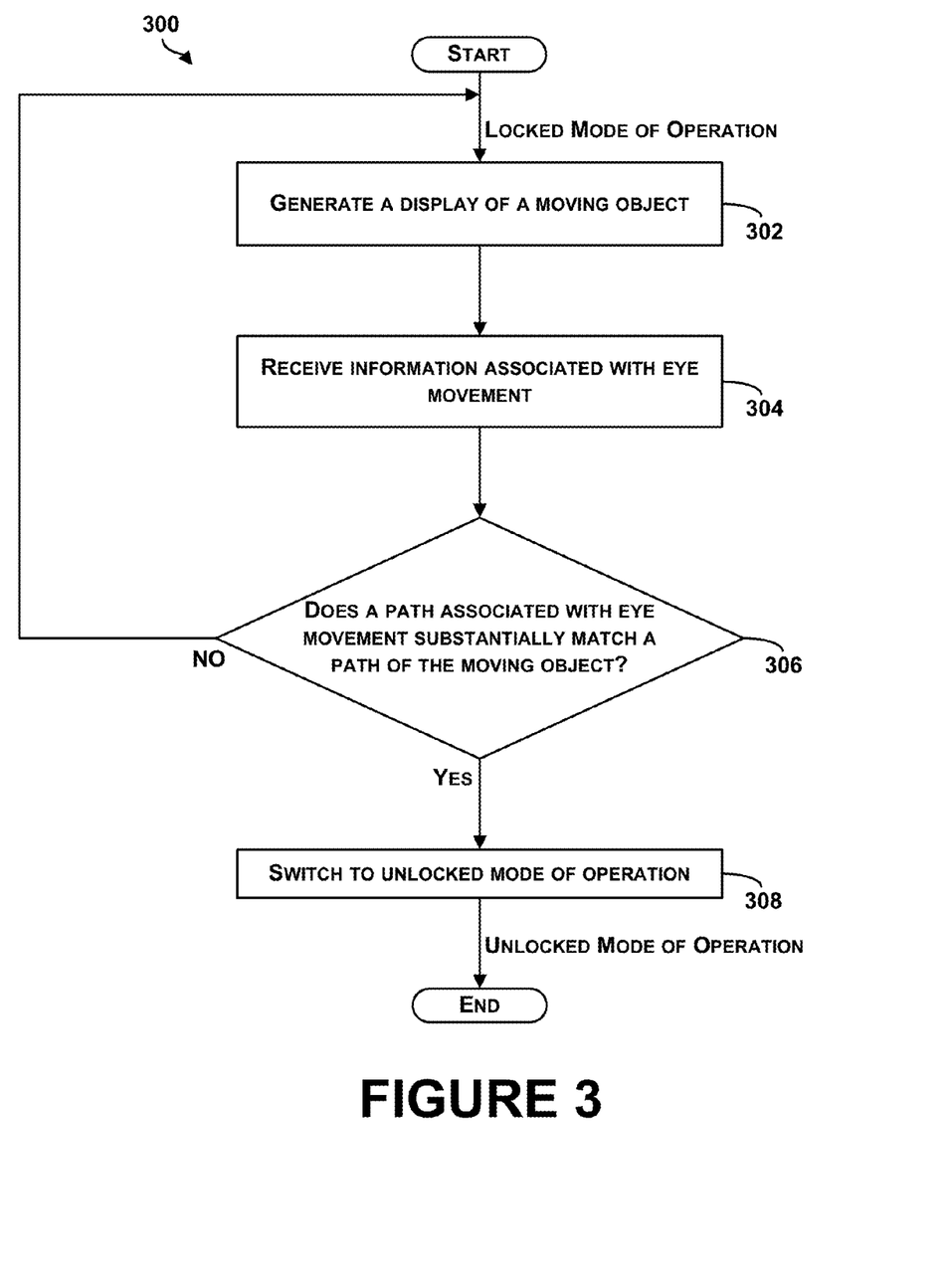
FIG. 3 is a flow chart of an example method to unlock a display screen using eye tracking information.
Figure 4:
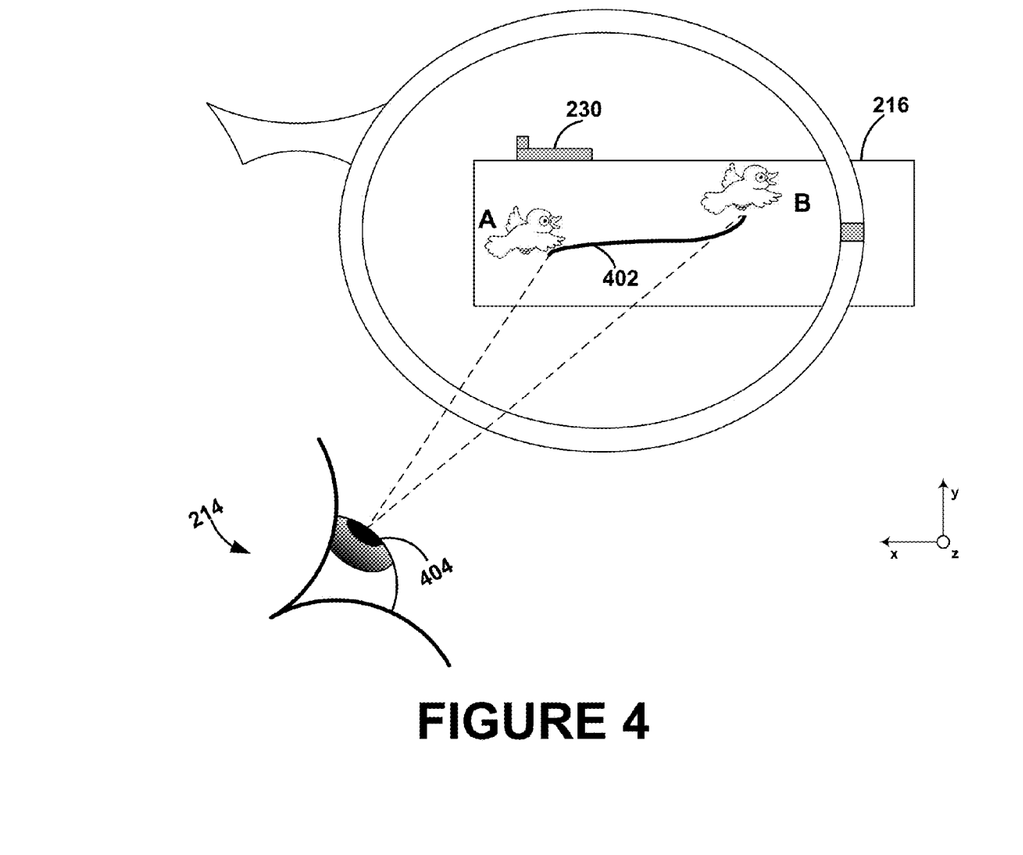
FIG. 4 is a diagram illustrating the example method to unlock a display screen using eye tracking information depicted in FIG. 3.

FIG. 3 is a flow chart illustrating an example method 300 for unlocking a screen using eye tracking information. FIG. 4 is a diagram illustrating the example method 300 to unlock a display screen using eye tracking information as depicted in FIG. 3, in accordance with at least some embodiments of the present disclosure. FIGS. 3 and 4 will be described together.

FIGS. 3 and 4 illustrate the method 300 in a context of a wearable computing system including a head-mounted display integrated into eyeglasses. However, the method applies to any computing system for unlocking a screen coupled to the computing system using eye tracking information.

Method 300 may include one or more operations, functions, or actions as illustrated by one or more of blocks 302, 304, 306, and 308. Although the blocks are illustrated in a sequential order, these blocks may in some instances be performed in parallel, and/or in a different order than those described herein. Also, the various blocks may be combined into fewer blocks, divided into additional blocks, and/or removed based upon the desired implementation In addition, for the method 300 and other processes and methods disclosed herein, the flowchart shows functionality and operation of one possible implementation of present embodiments. In this regard, each block may represent a module, a segment, or a portion of program code, which includes one or more instructions executable by a processor for implementing specific logical functions or steps in the process. The program code may be stored on any type of computer readable medium, for example, such as a storage device including a disk or hard drive. The computer readable medium may include a non-transitory computer readable medium, for example, such as computer-readable media that stores data for short periods of time like register memory, processor cache and Random Access Memory (RAM). The computer readable medium may also include non-transitory media or memory, such as secondary or persistent long term storage, like read only memory (ROM), optical or magnetic disks, compact-disc read only memory (CD-ROM), for example. The computer readable media may also be any other volatile or non-volatile storage systems. The computer readable medium may be considered a computer readable storage medium, a tangible storage device, or other article of manufacture, for example.

In addition, for the method 300 and other processes and methods disclosed herein, each block in FIG. 3 may represent circuitry that is wired to perform the specific logical functions in the process.

A wearable computing system including a head-mounted display (HMD) may operate in a locked mode of operation after a period of inactivity by a wearer. The locked mode of operation may include locking a display screen coupled to the HMD and a reduction in a functionality of the wearable computing system to save power.

At block 302, method 300 includes generate a display of a moving object. The wearer may attempt to activate the wearable computing system and unlock the display screen after the period of inactivity. The wearable computing system may not include a mouse or a convenient keyboard that may allow the wearer to unlock the display screen and switch the wearable computing system to an unlocked mode of operation. A processor coupled to the wearable computing system may generate the display of the moving object on the display screen of the HMD. The display of the moving object may be randomly generated by the processor. For example, a random display generated by the processor may comprise a different object and a different path of motion every time the processor generates the display of the moving object after a period of inactivity by the wearer. The processor may render a path of the moving object on the display. In one example, a size of the moving object may change (e.g., shrink) while the moving object may be moving on the display screen. By shrinking the size of the moving object, for example, the processor may determine with greater accuracy that the wearer may be tracking the moving object.

FIG. 4 illustrates the HMD integrated into eyeglasses. FIG. 4 shows the right side of the eyeglasses for illustration. However, the method 300 may apply to both left and right sides. The HMD integrated into the eyeglasses in FIG. 4 may, for example, be the HMD described in FIG. 2.

In FIG. 4, on a display of the optical system 216, the processor of the wearable computing system may generate a display of a moving object such as a bird moving from point A to point B through a path 402, for example. The processor may display the bird moving at a speed that may match an ability of a human eye to follow the moving object without saccades. Saccades include rapid eye movement that may disturb the eye tracking system 230, or may cause the eye tracking system 230 to determine a path of eye movement with less accuracy. In another example, the processor may display the bird moving at any speed and the eye tracking system 230 may not be disturbed.

In some examples, eyes may not look at a scene in fixed steadiness; instead, the eyes may move around to locate interesting parts of the scene and may build up a mental three-dimensional map corresponding to the scene. One reason for saccadic movement of an eye may be that a central part of the retina—known as the fovea—plays a role in resolving objects. By moving the eye so that small parts of the scene can be sensed with greater resolution, body resources can be used more efficiently. Eye saccades may be fast if the eye is attempting to follow an object that is moving with a speed that exceeds a certain predetermined speed. Once saccades start, fast eye movement may not be altered or stopped. Saccades may take 200 milliseconds (ms) to initiate, and then may last from 20-200 ms, depending on amplitude of the saccades (e.g., 20-30 ms is typical in language reading). Saccades may disturb or hinder an ability of the eye tracking system 230 to track eye movement. To prevent such disturbance to the eye tracking system 230, the processor may generate the display of the moving object such that the speed of the moving object may be below a predetermined threshold speed. If the speed exceeds the predetermined threshold speed, saccades may be stimulated. Consequently, the eye tracking system 230 may be disturbed and a performance of the eye tracking system 230 may deteriorate. In this case, the eye tracking system may not be able to accurately track eye movement or eye pupil movement of the wearer of the wearable computing system.

At block 304, method 300 includes receive information associated with eye movement. For example, in FIG. 4, the eye tracking system 230 may track eye movement of the eye 214 of the wearer. The eye tracking system 230 may, for example, track movements of an eye pupil 404. As the eye 214 or eye pupil 404 moves, the eye tracking system 230 may track a path associated with the eye 214 or the eye pupil 404 movement. The processor coupled to the wearable computing system may receive the information associated with the path associated with the eye movement from the eye tracking system 230.

In one example, the eye tracking system 230 may be continuously enabled to monitor an eye 214 of the wearer. In another example, the eye tracking system 230 may be disabled until another sensor or input to the wearable computing system may indicate an attempt by the wearer to unlock the screen. For example, the wearer may perform a gesture such as head tilt or head shake. A gyroscope coupled to the wearable computing system may detect such gesture. The processor coupled to the wearable computing system may receive information associated with the gyroscope indicating the gesture and may interpret the gesture as an attempt by the wearer to unlock the display and activate the wearable computing system. As another example, the wearer may press a button coupled to the wearable computing system to indicate an attempt to unlock the display and activate the wearable computing system. Upon detecting the attempt, the processor may enable the eye tracking system 230. As yet another example, a low power reflectivity sensor system that detects if the eye pupil 404 may be pointing or gazing at the screen may be used to detect the attempt. The low power reflectivity sensor system may include an infrared (IR) light emitting diode (LED) and photo detector that may be directed at the eye pupil 404. When the eye pupil 404 may be gazing at the IR LED to attempt to unlock the screen, the amount of IR light reflected back to the photo detector may drop, for example. Using another sensor, a gesture, a button, or the amount of IR light reflected back to the photo detector to indicate the attempt and consequently enabling the eye tracking system 230 may save power since the eye tracking system 230 may not be running continuously.

At decision block 306, method 300 determines whether a path associated with the eye movement substantially matches a path of the moving object or not. Based on the information associated with eye movement, the processor coupled to the wearable computing system may compare the path 402 of the moving object generated by the processor to the path associated with the eye movement. In some examples, the processor may adjust the path associated with the eye movement of the wearer before comparing the path associated with the eye movement to the path 402 of the moving object. For example, placement of eyeglasses including the wearable computing system and the HMD on ears and a nose of the wearer may be slightly different every time the wearer wears the eyeglasses after taking the eyeglasses off. A relative location of the eye 214 with respect to a camera coupled to the eye tracking system 230 or a relative location of a gaze axis associated with the eye 214 with respect to a reference axis associated with the HMD, for example, may vary. Therefore, the processor may apply a transform to the path associated with the eye movement to compensate for a difference in the relative location. The transform may, for example, include an offset of the path associated with the eye movement to compensate for a shift in the gaze axis of the eye 214 of the wearer of the HMD with respect to the reference axis associated with the HMD. The transform may comprise a rotational adjustment to compensate for a rotation in the gaze axis of the eye 214 of the wearer of the HMD with respect to the reference axis associated with the HMD.

At block 308, method 300 includes switch to unlocked mode of operation. If the path associated with the eye movement or eye pupil movement of the wearer matches or substantially matches the path 404 of the moving object, possibly after applying calibration data to the path associated with the eye movement, the wearable computing system may switch to be in an unlocked mode of operation. The unlocked mode of operation may comprise unlocking the display screen of the HMD and may comprise increasing the functionality of the wearable computing system.

If the path associated with the eye movement or eye pupil movement of the wearer does not match or does not substantially match the path 404 of the moving object, the wearable computing system may remain operable to be in the locked mode of operation.

In another example, generating a display of a moving object on a HMD and tracking eye movement of a wearer of the HMD may be used to calibrate the eye tracking system. As described in method 300, placement of eyeglasses including the HMD on ears and a nose of the wearer may be slightly different every time the wearer wears the eyeglasses after taking the eyeglasses off. A relative location of the eye with respect to a camera coupled to the eye tracking system or a relative location of a gaze axis associated with the eye with respect to a reference axis associated with the HMD, for example, may vary. A processor coupled to the HMD may calibrate the eye tracking system using the relative location of the gaze axis associated with the eye with respect to the reference axis associated with the HMD.

To calibrate the eye tracking system, the processor may initiate calibration procedures. The processor may, for example, generate the display of the moving object on the HMD and may prompt the wearer to follow the moving object with an eye or both eyes of the wearer. The processor may receive information associated with eye movement of the wearer through the eye tracking system. The processor may determine if a path associated with the eye movement of the wearer substantially matches a path of the moving object displayed on the HMD. In one example, a size of the moving object may change (e.g., shrink) while the moving object may be moving on the display screen. By shrinking the size of the moving object, for example, the processor may determine with greater accuracy that the wearer may be tracking the moving object. If the path associated with the eye movement of the wearer does not substantially match the path of the moving object displayed on the HMD, the processor may determine the relative location of the gaze axis associated with the eye with respect to the reference axis associated with the HMD.

The processor may apply a transform to the path associated with the eye movement to compensate for a difference in the relative location. The transform may, for example, include an offset of the path associated with the eye movement to compensate for a shift in the gaze axis of the eye of the wearer of the HMD with respect to the reference axis associated with the HMD. The transform may also comprise a rotational adjustment to compensate for a rotation in the gaze axis of the eye of the wearer of the HMD with respect to the reference axis associated with the HMD. The transform may further comprise a scale factor that may compensate for a distance between a camera, coupled to the eye tracking system, monitoring the eye movement of the wearer, or a reference point on the HMD, and the eye of the wearer. As a position of the camera or the reference point changes (e.g., farther or closer to the eye of the wearer) the scale factor may compensate for the change in position of the camera or the reference point with respect to the eye of the wearer. After the processor may apply the transform to the path associated with the eye movement, the path associated with the eye movement may substantially match the path of the moving object.

Path adjustment and the transform associated with the path adjustment may be referred to as calibration data associated with a particular placement of the HMD on a head of the user. The offset and rotational adjustment of the transform may be referred to as calibration parameters. The calibration parameters may be determined to cause the path associated with the eye movement to substantially match the path of the moving object. When the wearer of the HMD may wear the HMD with the particular placement, the processor may apply the calibration data associated with the particular placement to the eye movement information received from the eye tracking system. The processor may store the calibration data including the calibration parameters associated with the path adjustment in a memory coupled to the HMD, for example. When the wearer may place the HMD in a different position and no calibration data may have been stored for the different position, the processor may initiate the calibration procedures to determine calibration data associated with the different position and may store the calibration data for future use, for example. In another example, calibration procedures may not be initiated for every new relative location of the gaze axis with respect to the reference axis. The processor may perform calculations, (e.g., interpolation or extrapolation) using stored calibration parameters to determine calibration parameters associated with a new placement of the HMD.

Alternative to prompting the wearer to go through the calibration procedure as standalone procedures, the processor may use information associated with the wearer attempting unlocking the screen, as described in the method 300 for example, to calibrate the eye tracking system. Therefore, calibration of the eye tracking system may be integral to or a byproduct of unlocking the HMD.

Figure 5:
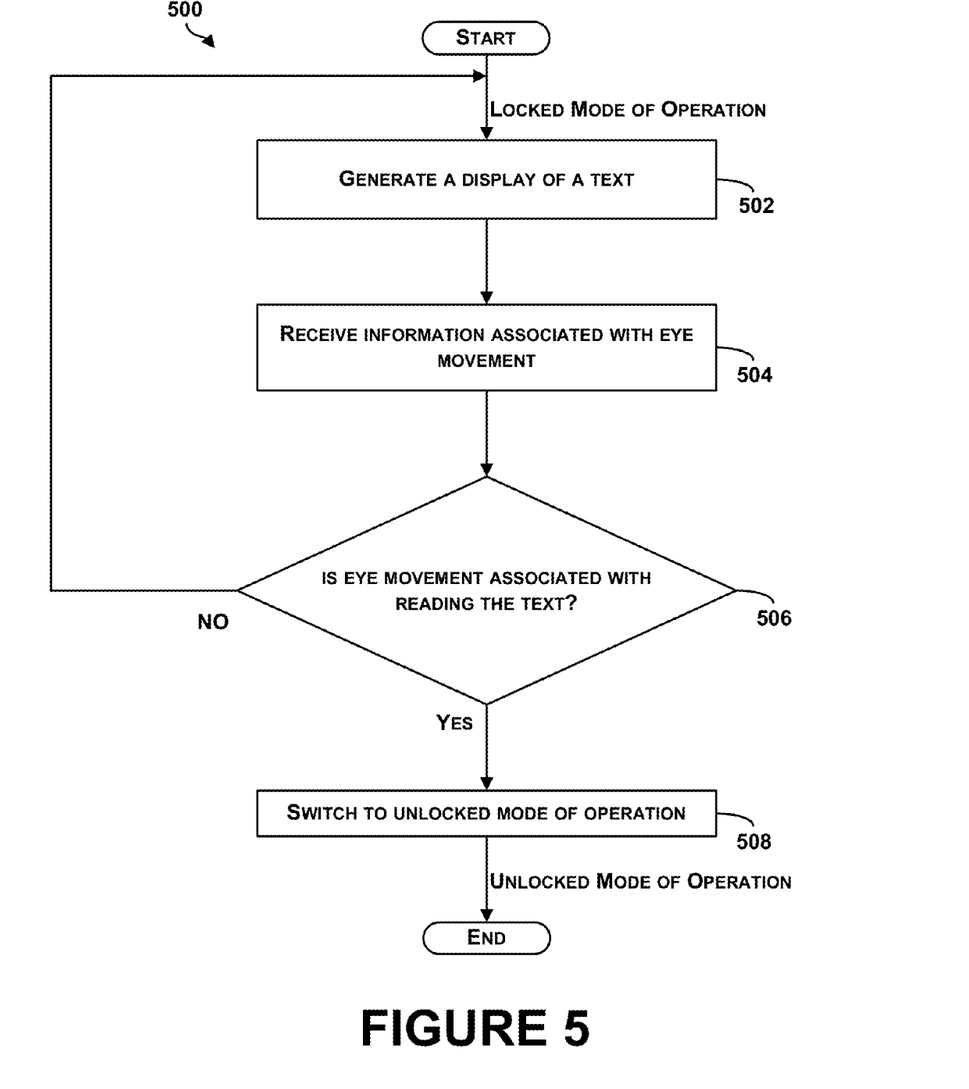
FIG. 5 is a flow chart of another example method to unlock a display screen using eye tracking information.
Figure 6:
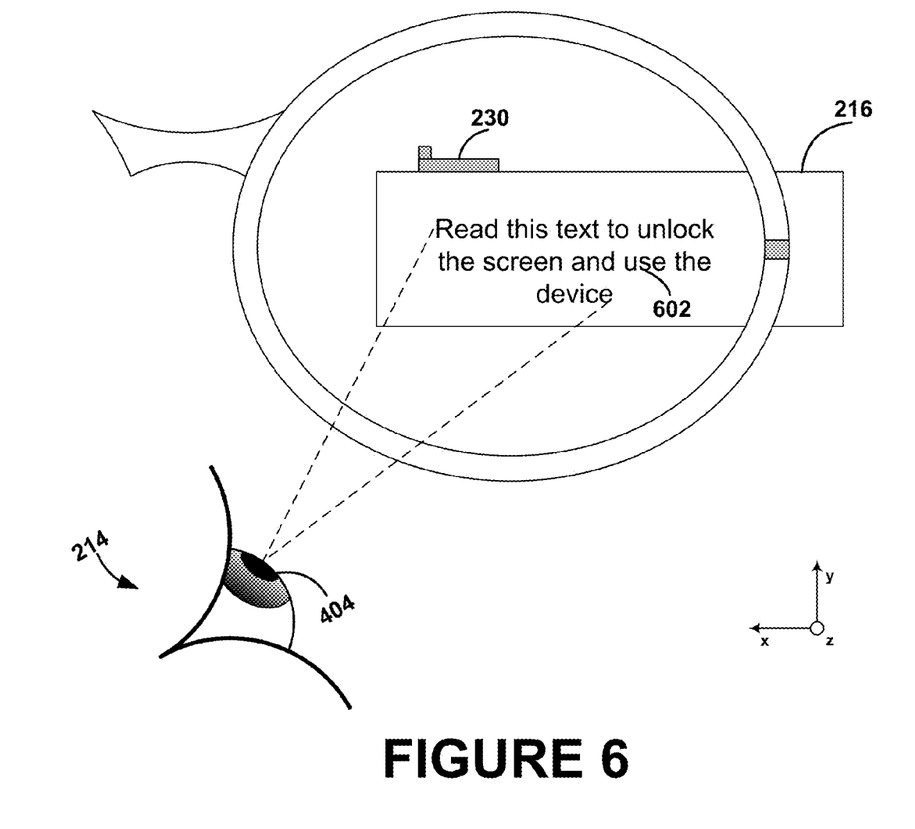
FIG. 6 is a diagram illustrating the example method to unlock a display screen using eye tracking information depicted in FIG. 5.

FIG. 5 is a flow chart illustrating another example method 500 for unlocking a screen using eye tracking information. FIG. 6 is a diagram illustrating the example method 500 to unlock a display screen using eye tracking information depicted in FIG. 5, in accordance with at least some embodiments of the present disclosure. FIGS. 5 and 6 will be described together.

Method 500 also starts with the wearable computing system including the HMD operating in a locked mode of operation after a period of inactivity by the wearer.

At block 502, method 500 includes generate a display of a text. The wearer may attempt to activate the wearable computing system and unlock the display screen after the period of inactivity. The wearable computing system may not include a mouse or a convenient keyboard that may allow the wearer to unlock the display screen and switch the wearable computing system to an unlocked mode of operation. A processor coupled to the wearable computing system may generate the display of the text on the display screen of the HMD. The display of the text may be randomly generated by the processor. A random display generated by the processor may comprise a different text every time the processor generates the display of the text.

FIG. 6 illustrates the HMD integrated into eyeglasses. FIG. 6 shows the right side of the eyeglasses for illustration. However, the method 500 may apply to both left and right sides. The HMD integrated into the eyeglasses in FIG. 6 may, for example, be the HMD described in FIGS. 2 and 4.

In FIG. 6, on a display of the optical system 216, the processor of the wearable computing system may generate a display of a text 602, for example. The processor may determine a spatial-temporal pattern of gaze locations associated with reading the text on the display. For example, an eye of a human reading the text may move at a given pace that may vary from one person to another. The eye or eyes of the wearer may move from left to right to read the text. The processor may randomly generate the text and an associated spatial-temporal pattern that corresponds to reading the text. Temporal characteristics of reading the text may be flexible or comprise a range of time to compensate for a difference in a reading pace from one person to another.

At block 504, method 500 includes receive information associated with eye movement. For example, in FIG. 6, the eye tracking system 230 may track eye movement of the eye 214 of the wearer. The eye tracking system 230 may, for example, track movements of an eye pupil 404. As the eye 214 or eye pupil 404 moves, the eye tracking system 230 may associate spatial-temporal characteristics to gaze movements of the eye pupil 404, for example. The processor coupled to the wearable computing system may receive the information associated with spatial-temporal characteristics of gaze movements of the eye pupil 404.

At decision block 506, method 500 determines whether eye movement is associated with reading the text or not. The processor coupled to the wearable computing system may compare a predetermined spatial-temporal pattern of gaze locations associated with reading the text generated by the processor to the spatial-temporal characteristics of gaze movements of the eye pupil 404 received from the eye tracking system 230.

At block 508, method 500 includes switch to unlocked mode of operation. If the spatial-temporal characteristics of gaze movements of the eye pupil 404 matches or substantially matches the predetermined spatial-temporal pattern of gaze locations associated with reading the text generated by the processor, the wearable computing system may switch to an unlocked mode of operation. The unlocked mode of operation may comprise unlocking the display of the HMD and increasing the functionality of the wearable computing system.

If the spatial-temporal characteristics of gaze movements of the eye pupil 404 does not match or does not substantially match the predetermined spatial-temporal pattern of gaze locations associated with reading the text generated by the processor, the wearable computing system may remain in the locked mode of operation.

IV. Example Systems and Computer Program Products

Figure 7:
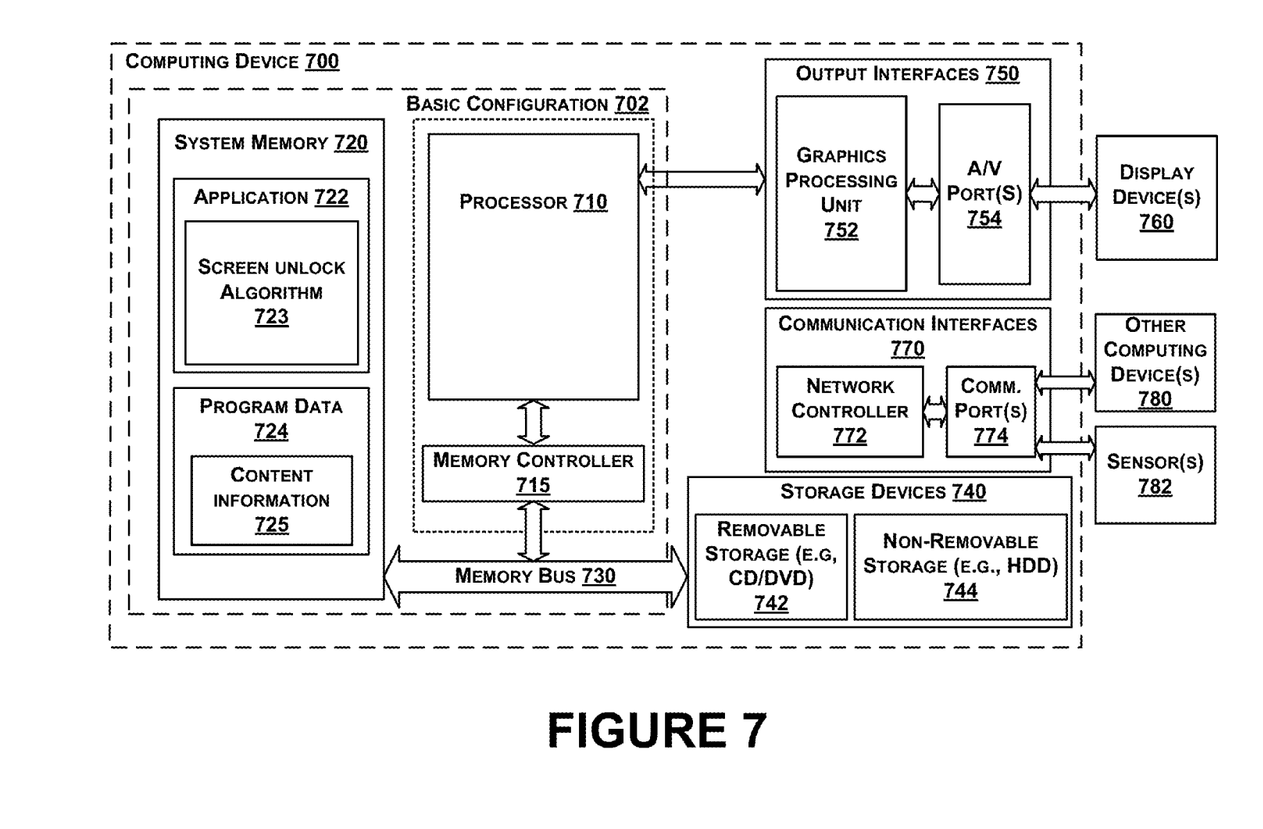
FIG. 7 is a functional block diagram illustrating an example computing device used in a computing system that is arranged in accordance with at least some embodiments described herein.

FIG. 7 is a functional block diagram illustrating an example computing device 700 used in a computing system that is arranged in accordance with at least some embodiments described herein. The computing device may be a personal computer, mobile device, cellular phone, video game system, or global positioning system, and may be implemented as a client device, a server, a system, a combination thereof, or as a portion of components described in FIGS. 1, 3, and 5. In a basic configuration 702, computing device 700 may include one or more processors 710 and system memory 720. A memory bus 730 can be used for communicating between the processor 710 and the system memory 720. Depending on the desired configuration, processor 710 can be of any type including but not limited to a microprocessor (μP), a microcontroller (μC), a digital signal processor (DSP), or any combination thereof. A memory controller 715 can also be used with the processor 710, or in some implementations, the memory controller 715 can be an internal part of the processor 710.

Depending on the desired configuration, the system memory 720 can be of any type including but not limited to volatile memory (such as RAM), non-volatile memory (such as ROM, flash memory, etc.) or any combination thereof. System memory 720 may include one or more applications 722, and program data 724. Application 722 may include screen unlock algorithm 723 that is arranged to provide inputs to the electronic circuits, in accordance with the present disclosure. Program Data 724 may include content information 725 that could be directed to any number of types of data. In some example embodiments, application 722 can be arranged to operate with program data 724 on an operating system.

Computing device 700 can have additional features or functionality, and additional interfaces to facilitate communications between the basic configuration 702 and any devices and interfaces. For example, data storage devices 740 can be provided including removable storage devices 742, non-removable storage devices 744, or a combination thereof. Examples of removable storage and non-removable storage devices include magnetic disk devices such as flexible disk drives and hard-disk drives (HDD), optical disk drives such as compact disk (CD) drives or digital versatile disk (DVD) drives, solid state drives (SSD), and tape drives to name a few. Computer storage media can include volatile and nonvolatile, non-transitory, removable and non-removable media implemented in any method or technology for storage of information, such as computer readable instructions, data structures, program modules, or other data.

System memory 720 and storage devices 740 are examples of computer storage media. Computer storage media includes, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by computing device 700. Any such computer storage media can be part of device 700.

Computing device 700 can also include output interfaces 750 that may include a graphics processing unit 752, which can be configured to communicate to various external devices such as display devices 760 or speakers via one or more A/V ports 754 or a communication interface 770. The communication interface 770 may include a network controller 772, which can be arranged to facilitate communications with one or more other computing devices 780 and one or more sensors 782 over a network communication via one or more communication ports 774. The one or more sensors 782 are shown external to the computing device 500, but may also be internal to the device. The communication connection is one example of a communication media. Communication media may be embodied by computer readable instructions, data structures, program modules, or other data in a modulated data signal, such as a carrier wave or other transport mechanism, and includes any information delivery media. A modulated data signal can be a signal that has one or more of its characteristics set or changed in such a manner as to encode information in the signal. By way of example, and not limitation, communication media can include wired media such as a wired network or direct-wired connection, and wireless media such as acoustic, radio frequency (RF), infrared (IR) and other wireless media.

Computing device 700 can be implemented as a portion of a small-form factor portable (or mobile) electronic device such as a cell phone, a personal data assistant (PDA), a personal media player device, a wireless web-watch device, a personal headset device, an application specific device, or a hybrid device that include any of the above functions. Computing device 700 can also be implemented as a personal computer including both laptop computer and non-laptop computer configurations.

Figure 8:
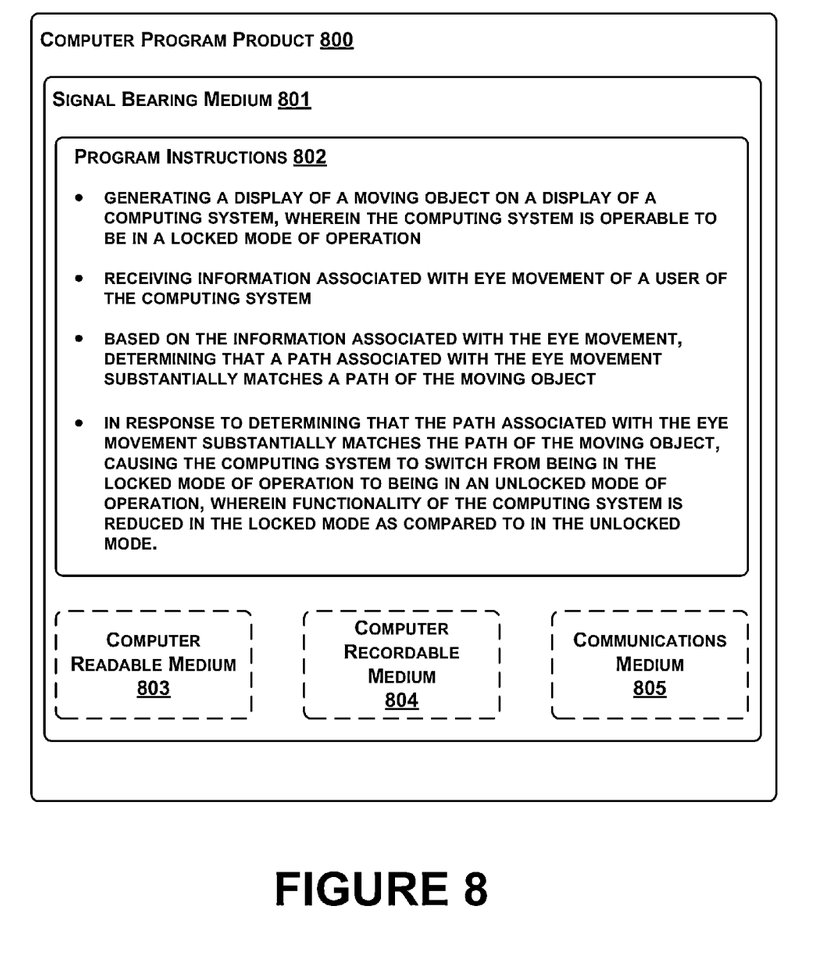
FIG. 8 is a schematic illustrating a conceptual partial view of an example computer program product that includes a computer program for executing a computer process on a computing device, arranged according to at least some embodiments presented herein.

In some embodiments, the disclosed methods may be implemented as computer program instructions encoded on a computer-readable storage media in a machine-readable format, or on other non-transitory media or articles of manufacture. FIG. 8 is a schematic illustrating a conceptual partial view of an example computer program product 800 that includes a computer program for executing a computer process on a computing device, arranged according to at least some embodiments presented herein. In one embodiment, the example computer program product 800 is provided using a signal bearing medium 801. The signal bearing medium 801 may include one or more program instructions 802 that, when executed by one or more processors may provide functionality or portions of the functionality described above with respect to FIGS. 1-7. Thus, for example, referring to the embodiments shown in FIGS. 3 and 5, one or more features of blocks 302-308 and/or blocks 502-508 may be undertaken by one or more instructions associated with the signal bearing medium 801. In addition, the program instructions 802 in FIG. 8 describe example instructions as well.

In some examples, the signal bearing medium 801 may encompass a computer-readable medium 803, such as, but not limited to, a hard disk drive, a Compact Disc (CD), a Digital Video Disk (DVD), a digital tape, memory, etc. In some implementations, the signal bearing medium 801 may encompass a computer recordable medium 804, such as, but not limited to, memory, read/write (R/W) CDs, R/W DVDs, etc. In some implementations, the signal bearing medium 801 may encompass a communications medium 805, such as, but not limited to, a digital and/or an analog communication medium (e.g., a fiber optic cable, a waveguide, a wired communications link, a wireless communication link, etc.). Thus, for example, the signal bearing medium 801 may be conveyed by a wireless form of the communications medium 805 (e.g., a wireless communications medium conforming with the IEEE 802.11 standard or other transmission protocol).

The one or more programming instructions 802 may be, for example, computer executable and/or logic implemented instructions. In some examples, a computing device such as the computing device 700 of FIG. 7 may be configured to provide various operations, functions, or actions in response to the programming instructions 802 conveyed to the computing device 700 by one or more of the computer readable medium 803, the computer recordable medium 804, and/or the communications medium 805. It should be understood that arrangements described herein are for purposes of example only. As such, those skilled in the art will appreciate that other arrangements and other elements (e.g. machines, interfaces, functions, orders, and groupings of functions, etc.) can be used instead, and some elements may be omitted altogether according to the desired results. Further, many of the elements that are described are functional entities that may be implemented as discrete or distributed components or in conjunction with other components, in any suitable combination and location.

While various aspects and embodiments have been disclosed herein, other aspects and embodiments will be apparent to those skilled in the art. The various aspects and embodiments disclosed herein are for purposes of illustration and are not intended to be limiting, with the true scope being indicated by the following claims, along with the full scope of equivalents to which such claims are entitled. It is also to be understood that the terminology used herein is for the purpose of describing particular embodiments only, and is not intended to be limiting.

What is claimed is:

1. A method comprising:
receiving eye tracking information associated with eye movement of a user of a computing system from an eye tracking system coupled to the computing system, wherein the computing system is in a first mode of operation;
based on the eye tracking information, determining that a path associated with the eye movement substantially matches a path of a displayed moving object, wherein determining that the path associated with the eye movement substantially matches the path of the displayed moving object comprises adjusting the path associated with the eye movement based on a location of a gaze axis of an eye with respect to a reference axis associated with the eye tracking system; and
in response to determining that the path associated with the eye movement substantially matches the path of the displayed moving object, causing the computing system to enter a second mode of operation, wherein the second mode of operation comprises a state of increased responsiveness to user-input as compared to the first mode of operation.

2. The method of claim 1, wherein the computing system includes a wearable computing system.

3. The method of claim 2, further comprising rendering the displayed moving object on a head-mounted display (HMD) coupled to the wearable computing system.

4. The method of claim 1, wherein adjusting the path associated with the eye movement comprises applying a transform to the path associated with the eye movement, and wherein the transform comprises an offset associated with a shift in the gaze axis of the eye with respect to the reference axis associated with the eye tracking system.

5. The method of claim 1, wherein adjusting the path associated with the eye movement comprises applying a transform to the path associated with the eye movement, and wherein the transform comprises a rotational adjustment associated with a rotation in the gaze axis of the eye with respect to the reference axis associated with the eye tracking system.

6. The method of claim 1, wherein the eye movement comprises eye-pupil movement, wherein determining that the path associated with the eye movement substantially matches the path of the displayed moving object comprises determining that a path associated with the eye-pupil movement substantially matches the path of the displayed moving object.

7. The method of claim 1, further comprising:
receiving mode information indicating an attempt to change a mode of operation of the computing system from the first mode of operation to the second mode of operation; and
enabling the eye tracking system, based on the mode information.

8. The method of claim 1, wherein the eye tracking system comprises at least one sensor configured to monitor the eye movement.

9. The method of claim 1, wherein the path of the displayed moving object is randomly generated by the computing system.

10. A non-transitory computer readable medium having stored thereon instructions executable by a computing device to cause the computing device to perform functions comprising:
receiving eye tracking information associated with eye movement of a user of the computing device from an eye tracking system coupled to the computing device, wherein the computing device is in a first mode of operation;
based on the eye tracking information, determining that a path associated with the eye movement substantially matches a path of a displayed moving object, wherein determining that the path associated with the eye movement substantially matches the path of the displayed moving object comprises adjusting the path associated with the eye movement based on a location of a gaze axis of an eye with respect to a reference axis associated with the eye tracking system; and in response to determining that the path associated with the eye movement substantially matches the path of the displayed moving object, causing the computing device to enter a second mode of operation, wherein the second mode of operation comprises a state of increased responsiveness to user-input as compared to the first mode of operation.

11. The non-transitory computer readable medium of claim 10, wherein the computing device includes a wearable computer, and wherein the instructions are further executable by the computing device to cause the computing device to perform functions comprising causing a head-mounted display coupled to the wearable computer to render the displayed moving object.

12. The non-transitory computer readable medium of claim 10, wherein the instructions are further executable by the computing device to cause the computing device to perform functions comprising:

receiving mode information indicating an attempt to change a mode of operation of the computing device from the first mode of operation to the second mode of operation; and enabling the eye tracking system, based on the mode information.

13. The non-transitory computer readable medium of claim 12, wherein the function of receiving the mode information indicating the attempt comprises receiving gesture information associated with head motion.

14. The non-transitory computer readable medium of claim 10, wherein adjusting the path associated with the eye movement comprises applying a transform to the path associated with the eye movement, wherein the transform includes one or more of: (i) an offset associated with a shift in the gaze axis with respect to the reference axis associated with the eye tracking system, (ii) a rotational adjustment associated with a rotation in the gaze axis of the eye with respect to the reference axis, and (iii) a scale factor associated with a distance between the eye of the user and a reference point on the eye tracking system.

15. The non-transitory computer readable medium of claim 14, wherein the offset, the rotational adjustment, and the scale factor are stored on the computing device as calibration parameters, and wherein the calibration parameters are associated with causing the path associated with the eye movement of the user to substantially match the path of the displayed moving object.

16. A system comprising:

a wearable computer including a head-mounted display (HMD), wherein the wearable computer is operable to be in a first mode of operation;

an eye tracking system in communication with the wearable computer, wherein the eye tracking system is configured to track eye movement of a user of the wearable computer; and a processor coupled to the wearable computer and in communication with the eye tracking system, wherein the processor is configured to:

receive eye tracking information associated with the eye movement from the eye tracking system, wherein the processor is configured to adjust the eye tracking information based on a location of a gaze axis of an eye with respect to a reference axis associated with the HMD;

based on the eye tracking information, determine that the eye movement is associated with reading a text displayed on the HMD; and in response to determining that the eye movement is associated with reading the text, cause the wearable computer to enter a second mode of operation, wherein the second mode of operation comprises a state of increased responsiveness to user-input as compared to the first mode of operation.

17. The system of claim 16, wherein the processor is configured to determine that the eye movement is associated with reading the text by determining that gaze movements associated with the eye movement substantially match a predetermined spatial-temporal pattern of gaze locations associated with reading the text displayed on the HMD.

18. The system of claim 16, wherein the processor is further configured to:

receive mode information indicative of an attempt to change a mode of operation of the wearable computer from the first mode of operation to the second mode of operation; and enable, based on the mode information, the eye tracking system so as to receive the eye tracking information associated with the eye movement from the eye tracking system.

19. The system of claim 18, further comprising a sensor coupled to the wearable computer, wherein the processor is configured to receive, from the sensor, the mode information indicative of the attempt to change the mode of operation of the wearable computer.

* * * * *